United States Patent
Hirota et al.

(10) Patent No.: US 7,126,023 B2
(45) Date of Patent: Oct. 24, 2006

(54) METHOD FOR DEUTERATION OF AN INERT METHYLENE

(75) Inventors: Kosaku Hirota, Gifu (JP); Hironao Sajiki, Gifu (JP)

(73) Assignee: Wako Pure Chemical Industries, Ltd., Osaka (JP)

( * ) Notice: Subject to any disclaimer, the term of this patent is extended or adjusted under 35 U.S.C. 154(b) by 0 days.

(21) Appl. No.: 10/516,638

(22) PCT Filed: Nov. 12, 2002

(86) PCT No.: PCT/JP02/11785

§ 371 (c)(1),
(2), (4) Date: Dec. 2, 2004

(87) PCT Pub. No.: WO03/104166

PCT Pub. Date: Dec. 18, 2003

(65) Prior Publication Data

US 2005/0177015 A1    Aug. 11, 2005

(30) Foreign Application Priority Data

Jun. 6, 2002 (JP) ............................. 2002-166224

(51) Int. Cl.
*C07C 69/76* (2006.01)
*C07C 53/134* (2006.01)
*C07C 41/00* (2006.01)

(52) U.S. Cl. ...................... 560/105; 562/496; 568/626; 568/715; 585/941

(58) Field of Classification Search ............... None
See application file for complete search history.

(56) References Cited

FOREIGN PATENT DOCUMENTS

| EP | 0 203 588 | 12/1986 |
|---|---|---|
| JP | 63-198638 | 8/1988 |
| JP | 10-139694 | 5/1998 |

OTHER PUBLICATIONS

Hirota et al, Bulletin of the Chemical Society of Japan, Differences in the Catalytic Activity of Nickel, Platinum and Palladium as Observed in the Isotopic Exchange Reaction of Paraxylene with Deuterium Oxide, 1962, 35, pp. 228-232.*
Rylander, Hydrogenation Methods, 985, Academic Press, Inc., Orlando, Florida, p. 4.*

* cited by examiner

*Primary Examiner*—Paul A. Zucker
(74) *Attorney, Agent, or Firm*—Hamre, Schumann, Mueller & Larson, P.C.

(57) ABSTRACT

The present invention relates to a method for deuteration of an inert alkane using activated palladium carbon. The present invention discloses "A method for deuteration of a hydrogen atom of a methyl group or a hydrogen atom bonded to a carbon atom at benzyl position and the other carbon atoms of an alkylene group having not less than 2 carbon atoms, in a compound containing the methyl group or the-alkylene group having not less than 2 carbon atoms, directly bonded to an aromatic ring which may have a substituent, which comprises placing said compound in a deuterated solvent in the presence of activated palladium carbon, under sealed reflux condition".

7 Claims, No Drawings

US 7,126,023 B2

METHOD FOR DEUTERATION OF AN INERT METHYLENE

TECHNICAL FIELD

The present invention relates to a method for deuteration of an inert alkane using activated palladium carbon.

BACKGROUND OF THE INVENTION

A compound labeled with an isotope is useful to examine in vivo kinetics of drug, in particular, a compound labeled with deuterium (D) is generally utilized for this purpose.

The compound labeled with deuterium has generally been synthesized by a conventional method using a preliminary deuterated starting material, however, said synthetic method has a problem with requiring multiple synthetic steps, so it is desired to develop a method for obtaining a compound labeled with deuterium by directly exchanging C—H of a final objective compound for C-D (H-D exchange).

The present inventors have conducted extensive study and have found a method for selective deuteration of only a hydrogen atom binded to a carbon atom directly bonded to an aromatic ring (a hydrogen atom at the benzyl position). However, said deuteration method provides still low deuteration rate of a hydrogen atom at terminal carbon even at benzyl position (a hydrogen atom of a methyl group directly bonded to an aromatic ring) and no deuteration of a hydrogen atom bonded to-a carbon atom other than at benzyl position. Therefore, it has been desired to develop a method for attaining high deuteration rate of a hydrogen atom of a methyl group directly bonded to an aromatic ring and also deuteration of a hydrogen atom bonded to a carbon atom other than at benzyl position.

Therefore, the purpose of the present invention is to develop a method for high deuteration rate of a hydrogen atom in a methyl group directly bonded to an aromatic ring and also an effective deuteration of not only a hydrogen atom at benzyl position but also a hydrogen atom bonded to the other carbon atoms.

SUMMARY OF THE INVENTION

The present inventors have studied extensively to solve the above-described problem and found that the reaction of a compound having a methyl group or an alkylene group, directly bonded to an aromatic ring which may have a substituent, and a deuterated solvent in the presence of an activated palladium carbon catalyst under sealed reflux condition can deuterate not only a hydrogen atom of said methyl group and said carbon atom bonded to at benzyl position, in said compound, but also a hydrogen atom bonded to a carbon atom other than at benzyl position in said compound, and finally the present invention has been completed on the basis of these findings. The present invention relates to;

A method for deuteration of a hydrogen atom of a methyl group or a hydrogen atom bonded to a carbon atom at benzyl position and the other carbon atoms of an alkylene group having not less than 2 carbon atoms, in a compound containing the methyl group or the alkylene group having not less than 2 carbon atoms, directly bonded to an aromatic ring which may have a substituent, which comprises placing said compound in a deuterated solvent in the presence of activated palladium carbon, under sealed reflux condition.

BEST MODE FOR CARRYING OUT THE INVENTION

In the compound containing a methyl group or an alkylene group having not less than 2 carbon atoms, directly bonded to an aromatic ring which may have a substituent, of the present invention, the compound containing a methyl group or an alkylene group having not less than 2 carbon atoms, directly bonded to an aromatic ring, includes for example, a compound represented by the general formula [1]:

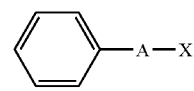

[1]

(wherein A is a methylene group or an alkylene group having not less than 2 carbon atoms; X is a hydrogen atom, an alkoxy group, a carboxyl group, a hydroxyl group, an amino group, an acyl group, an acylamino group or an alkoxycarbonyl group; and when A is a methylene group, X is a hydrogen atom.)

In the general formula [1], the alkylene group having not less than 2 carbon atoms, represented by A, may be straight chained, branched or cyclic, preferably straight chained or branched and more preferably straight chained, and includes one having generally 2 to 20, preferably 2 to 10 and more preferably 2 to 7 carbon atoms.

The specific example of the alkylene group having not less than 2 carbon atoms, represented by A, includes such as an ethylene group, a methylmethylene group, a n-propylene group, an isopropylene group, a n-butylene group, an isobutylene group, a 1,2-dimethylethylene group, a n-pentylene group, an isopentylene group, a 2-methylbutylene group, a 1,2-dimethylpropylene group, a n-hexylene group, an isohexylene group, a 2-methylpentylene group, a 1,4-dimethylbutylene group, a 2,3-dimethylbutylene group, a n-heptylene group, an isoheptylene group, a 1,2-dimethylpentylene group, a 1,2,3-trimethylbutylene group, an n-octylene group, a n-nonylene group, a n-decylene group, an n-undecylene group, a n-dodecylene group, a n-tridecylene group, a n-tetradecylene group, a n-pentadecylene group, a n-hexadecylene-group, a n-heptadecylene group, an n-octadecylene group, a n-nonadecylene group, an n-icosylene group, a cyclopentylene group, a cyclohexylene group, a cycloheptylene group, a cyclooctylene group, a cyclononylene group, a cyclodecylene group, a cycloundecylene group, a cyclododecylene group, a cyclotridecylene group, a cyclotetradecylene group, a cyclohexadecylene group, a cycloheptadecylene group, a cyclononadecylene group and a cycloicosylene group. Among others, the above-described alkylene group having not less than 5 carbon atoms may be substituted with an oxygen atom at fourth or more carbon atom from the carbon atom directly bonded to the aromatic ring thereof.

In the general formula [1], the alkoxy group represented by X includes one having generally 1 to 6 carbon atoms, preferably 1 to 4 carbon atoms, which is specifically exemplified by such as a methoxy group, an ethoxy group, a propoxy group, a butoxy group, a pentyloxy group and a hexyloxy group.

The carboxyl group represented by X may be a salt of an alkali metal such as sodium, potassium and lithium, and a salt of an alkaline earth metal such as calcium and magnesium, and among others, preferably an alkali metal salt because of easy handling, and more preferably a sodium salt.

The amino group represented by X includes a primary amino group (—NH$_2$), a secondary amino group (—NHR) and a tertiary amino group (—NR$_2$) (wherein R is an alkyl group having 1 to 6, preferably 1 to 4 carbon atoms) which is specifically exemplified by a primary amino group; a secondary amino group such as a methylamino group, an ethylamino group, a propylamino group, a butylamino group, a pentylamino group and a hexylamino group; and a tertiary amino group such as a dimethylamino group, a diethylamino group, a dipropylamino group, a dibutylamino group, a dipentylamino group and a dihexylamino group, and among others, a primary amino group is preferable.

The acyl group represented by X includes one derived from an aliphatic carboxylic acid having generally 2 to 10 carbon atoms such as an acetyl group, a propionyl group, a butyryl group, an isobutyryl group, a valeryl group, an isovaleryl group and a pivaloyl group; and one derived from an aromatic carboxylic acid such as a benzoyl group.

The acylamino group represented by X includes a group wherein —NH— bond is bonded further to the carbonyl group of the above acyl group, which is specifically exemplified by an acetylamino group, a propionylamino group, a butyrylamino group, an isobutyrylamino group, a valerylamino group, an isovalerylamino group, a pivaloylamino group and a benzoylamino group.

The alkoxycarbonyl group represented by X includes one having generally 2 to 7 carbon atoms, which is specifically exemplified by such as a methoxycarbonyl group, an ethoxycarbonyl group, a propoxycarbonyl group, a pentyloxycarbonyl group and a hexyloxycarbonyl group.

Further, when X is an alkoxy group, a hydroxyl group or an amino group, A is preferably a straight-chained alkylene group having not less than 3 carbon atoms.

Among the hydrogen atoms bonded to the aromatic ring in the compound represented by the general formula [1], generally 1 to 5, preferably 1 to 2, more preferably 1 hydrogen atom may be substituted each independently with such as an alkyl group, an aryl group, an aralkyl group, an alkoxy group, a nitro group and an amino group.

Further, the alkyl group when a hydrogen atom of an aromatic ring is substituted with an alkyl group may be straight chained or branched, preferably straight chained, and includes one having generally 1 to 10 carbon atoms, preferably 1 to 6 carbon atoms, which is specifically exemplified by a methyl group, an ethyl group, a n-propyl group, an isopropyl group, a n-butyl group, an isobutyl group, a sec-butyl group, a tert-butyl group, a n-pentyl group, an isopentyl group, a sec-pentyl group, a tert-pentyl -group, a neopentyl group, a n-hexyl group, an isohexyl group, a 2,2-dimethylbutyl group, a n-heptyl group, an isoheptyl group, a sec-heptyl group, a tert-heptyl group, an n-octyl group, an isooctyl group, a n-nonyl group, an isononyl group, a sec-nonyl group and a n-decyl group.

The aryl group when a hydrogen atom of an aromatic ring is substituted with an aryl group includes one having generally 6 to 14 carbon atoms, which is specifically exemplified by a phenyl group, a naphthyl group and an anthryl group.

The aralkyl group when a hydrogen atom of an aromatic ring is substituted with an aralkyl group includes one having generally 7 to 10 carbon atoms, which is specifically exemplified by such as a benzyl group, a phenylethyl group, a phenylpropyl group and a phenylbutyl group.

The alkoxy group when a hydrogen atom of an aromatic ring is substituted with an alkoxy group may be straight chained or branched, and includes one having generally 1 to 6 carbon atoms, preferably 1 to 4 carbon atoms, which is specifically exemplified by such as a methoxy group, an ethoxy group, a propoxy group, a butoxy group, a pentyloxy group and a hexyloxy group.

The amino group when a hydrogen atom of an aromatic ring is substituted with an amino group may be the same as examples of the amino group represented by X in the general formula [1] described above.

Among the compounds represented by the general formula [1], one having no substituent in the aromatic ring thereof is preferable.

The specific example of the compound represented by the above-described general formula [1] includes a compound having a methyl group directly bonded to the aromatic ring such as:

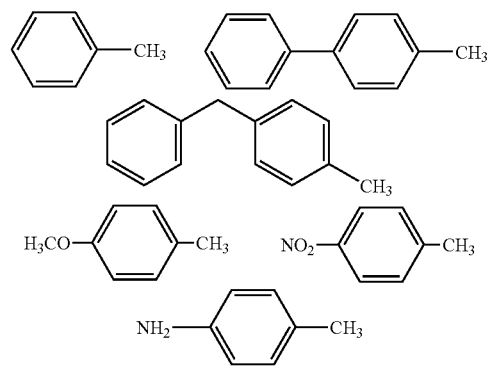

and a compound containing an alkylene group having not less than 2 carbon atoms directly bonded to the aromatic ring such as:

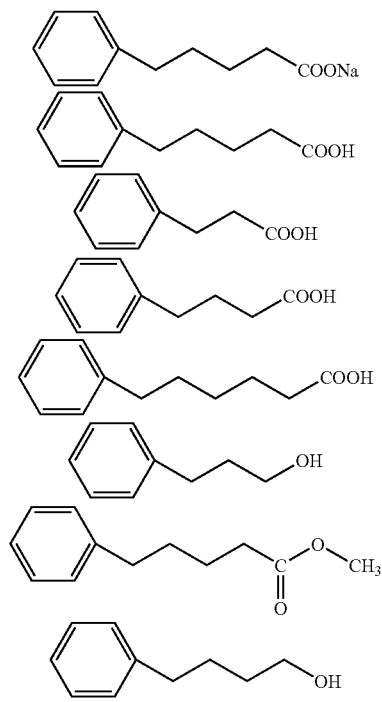

-continued

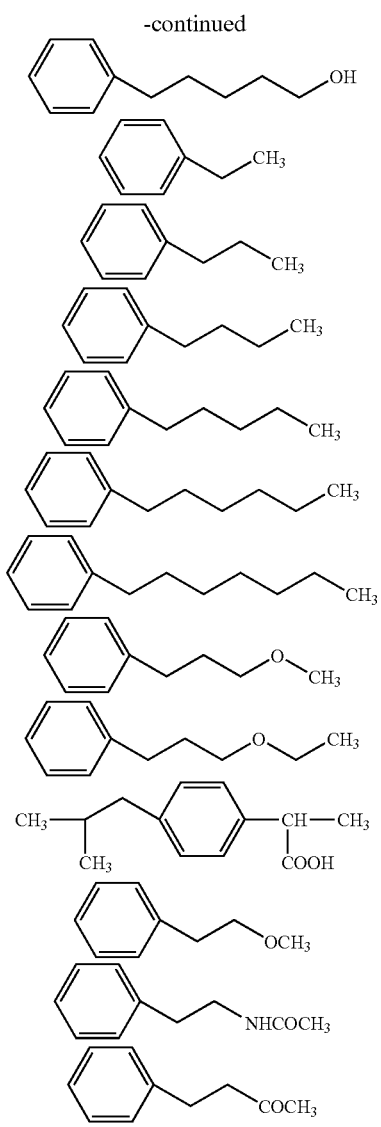

In the method for deuteration of the present invention, the activated palladium carbon used as a catalyst is such so-called "palladium carbon" as activated by contact with hydrogen gas.

In the method for deuteration of the present invention, as the activated palladium carbon, a palladium carbon preliminarily activated by for example, hydrogen gas may be used, or a non-activated palladium carbon can also be used if hydrogen gas is present in a deuteration reaction system.

An amount of the non-activated palladium carbon or activated palladium carbon to be used is generally 0.1 to 50% by weight, preferably 3 to 10% by weight, relative to the amount of the compound containing a methyl group or an alkylene group having not less than 2 carbon atoms directly bonded to the aromatic ring which may have a substituent, used as reaction substrate.

Further, in the case of using non-activated palladium carbon for the reaction of the present invention, use of too much hydrogen gas in the reaction system causes hydrogenation of a deuterated solvent and thus affects deuteration reaction itself of the present invention. Therefore, an appropriate amount of hydrogen gas is such quantity as necessary to activate palladium carbon, and an amount of hydrogen gas to be used is generally 1 to 20000, preferably 10 to 700 equivalents weight, relative to the amount of palladium in palladium carbon.

The specific example of a deuterated solvent to be used in the method for deuteration of the present invention includes deuterium oxide; deuterated alcohols such as deuterated methanol, deuterated ethanol, deuterated isopropanol, deuterated butanol, deuterated tert-butanol, deuterated pentanol, deuterated hexanol, deuterated heptanol, deuterated octanol, deuterated nonanol, deuterated decanol, deuterated undecanol and deuterated dodecanol; deuterated carboxylic acids such as deuterated formic acid, deuterated acetic acid, deuterated propionic acid, deuterated-butyric-acid, deuterated isobutyric acid, deuterated valeric acid, deuterated isovaleric acid and deuterated pivalic acids; deuterated ketones such as deuterated acetone, deuterated methyl ethyl ketone, deuterated methyl isobutyl ketone, deuterated diethyl ketone, deuterated dipropyl ketone, deuterated diisopropyl ketone and deuterated dibutyl ketone; and deuterated dimethylsulfoxide, and among others, deuterium oxide and deuterated methanol are preferable. These solvents may be ones deuterating at least one hydrogen atom in a molecular thereof, and specifically deuterated alcohols, wherein a hydrogen atom of a hydroxyl group is deuterated, or deuterated carboxylic acids, wherein a hydrogen atom of a carboxyl group is deuterated, can be used in the method for deuteration of the present invention. Among others, a solvent wherein all hydrogen atoms of a molecule thereof are deuterated is more preferable.

An amount of the deuterated solvent to be used is the amount so that generally 1 to 1000 equivalent weights, preferably 10 to 250 equivalent weights of deuterium atom is contained in said solvent, relative to the compound containing a methyl group or an alkylene group having not less than 2 carbon atoms directly bonded to an aromatic ring which may have a substituent, used as reaction substrate, if theoretical quantity of a deuterium atom required to replace a hydrogen atom at an exchange position is 1 equivalent weight.

A reaction temperature in the method for deuteration of the present invention may be set at generally not lower than boiling temperature (under normal pressure) of the solvent to retain refluxing state, preferably boiling temperature to boiling temperature +30° C., more preferably boiling temperature to boiling temperature +20° C. and further more preferably boiling temperature +5° C. to boiling temperature +15° C.

A sealed reaction system may be heated and/or pressurized to set reaction temperature described above, and-consequently attain pressurized state.

An inert gas such as nitrogen gas and argon gas may be used to pressurize a reaction system.

A reaction time is generally 1 to 100 hours, preferably 10 to 50 hours and more preferably 15 to 30 hours.

The method for deuteration of the present invention is concretely explained taking the case of using deuterium oxide as a solvent.

Namely, for example, in 1 ml of deuterium oxide are suspended 0.25 mmol of the compound (substrate) represented by the general formula [1] and about 10% by weight of non-activated palladium carbon (Pd 10%) relative to the amount of said substrate. Then, the atmosphere of the sealed reaction system is replaced with hydrogen gas, followed by reacting by heating under reflux for about 24 hours in an oil-bath. After completion of the reaction, the reaction solution is filtered to be subjected as it is to structural analysis by ¹H-NMR and mass spectrometry measurement, when the reaction product is soluble in deuterium oxide. When the reaction product is hardly soluble in deuterium oxide, the reaction product is isolated from the reaction solution to be subjected to structural analysis of the reaction product by ¹H-NMR and mass spectrometry measurement.

The isolation of the products from the reaction solution in the case of the products hardly soluble in deuterium oxide may be carried out according to a known purification method.

In a compound represented by the general formula [1], it is estimated that the deuteration of an -A-X group or a substituent of an aromatic ring can obtain high deuteration rate of a hydrogen atom bonded to a carbon atom closer to the aromatic ring.

Further, in the case that an oxygen atom is included in a group represented by an -A-X group or in an alkyl chain bonded to an aromatic ring as a substituent, it is difficult to deuterate a hydrogen atom bonded to a carbon atom next to said oxygen atom and a carbon atom located far from said oxygen atom viewed from the aromatic ring.

When the compound having a substituent such as a nitro group, among the compounds represented by the general formula [1], is used as a reaction substrate and hydrogen gas is used to activate a catalyst in a reaction system for deuteration reaction, a substituent such as nitro group of said substrate may be reduced to an amino group and the like in addition to deuteration of the present invention.

As mentioned above, a hydrogen atom of a methyl group directly bonded to an aromatic ring, which could be deuterated but at a low ratio by a conventional method, can be deuterated very effectively and also not only a hydrogen atom at a benzyl position in an alkylene group having not less than 2 carbon atoms but also a hydrogen atom other than at a benzyl position, which could not be deuterated by a conventional method, can be deuterated by a deuteration method of the present invention, characterized by reaction of substrate using an activated palladium carbon and a deuterated solvent under sealed reflux condition.

In the following, the present invention is explained in further detail referring to examples, but the present invention is not limited thereto by any means.

EXAMPLE

Example 1

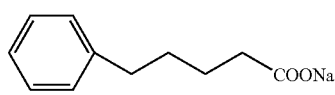

In 1 ml of deuterium oxide were suspended 0.25 mmol of a compound represented by the above mentioned formula, 10% by weight of palladium carbon (Pd 10%) relative to said compound, and 0.25 mmol of p-anisic acid as an internal standard, followed by replacing the atmosphere of a reaction system with hydrogen gas using a balloon and contacting the reaction solution with hydrogen gas. The reaction solution was heated at 110° C. for 24 hours in an oil-bath, followed by filtering with a membrane filter. The filtrate was subject as it is to structural analysis of products by ¹H-NMR and mass spectrometry measurement. The result showed that a hydrogen atom of the aromatic ring and a hydrogen atom of the alkylene group bonded to the aromatic ring, in raw material were deuterated. Deuteration rate (%) of each hydrogen atom bonded to a carbon atom in the compound is shown in Table 1.

TABLE 1

|  | Reaction temperature | Ph | C1 | C2 + C3 | C4 |
|---|---|---|---|---|---|
| Example 1 | 110° C. | 21 | 93 | 88 | 53 |
| Comparative Example 1 | Room temperature | 0 | 89 | 0 | 0 |

In the Table, "Ph" means a carbon atom in an aromatic ring, "C1", "C2+C3" and "C4" mean a carbon atom denoted by the number in the following formula, respectively. The numbers in the Table show deuteration rate of the hydrogen atom bonded to each carbon atom.

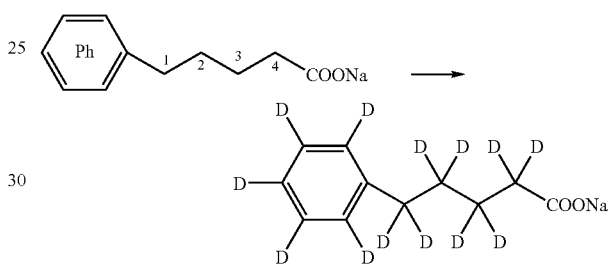

Comparative Example 1

Deuteration was carried out by the same procedure as in Example 1, except for carrying out the reaction at room temperature. Deuteration rate (%) of the hydrogen atom bonded to the carbon atom in the compound is shown in Table 1.

Comparative Examples 2 and 3

Deuteration was carried out by the same procedure as in Example 1 using substrate compounds without an aromatic ring, shown by the following formula, but deuteration of both compounds did not occur at all.

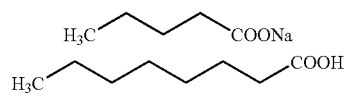

Examples 2 to 8

Deuteration was carried out by the same procedure as in Example 1, except for using the compounds shown in Table 2 as substrates. Deuteration rate (%) of the hydrogen atom bonded to the carbon atom in the compound is shown in Table 2.

TABLE 2

| substrate | Use Amount (mmol) | Ph | C1 | C2 | C3 | C4 | C5 | C6 | C7 |
|---|---|---|---|---|---|---|---|---|---|
| Exam. 2 | PhCH$_3$ | 5 | 0 | 64 | — | — | — | — | — | — |
| Exam. 3 | PhCH$_2$CH$_3$ | 4 | 0 | 59 | 52 | — | — | — | — | — |
| Exam. 4 | Ph(CH$_2$)$_2$CH$_3$ | 4 | 19 | 77 | 75 | 56 | — | — | — | — |
| Exam. 5 | Ph(CH$_2$)$_3$CH$_3$ | 3 | 51 | 74 | 75 | 72 | 70 | — | — | — |
| Exam. 6 | Ph(CH$_2$)$_4$CH$_3$ | 0.25 | 0 | 85 | 80 | 12 | 0 | — | — | — |
| Exam. 7 | Ph(CH$_2$)$_5$CH$_3$ | 0.25 | 32 | 90 | 96 | | 36 | | 11 | — |
| Exam. 8 | Ph(CH$_2$)$_6$CH$_3$ | 0.25 | 20 | 93 | 59 | | 17 | | | 10 |

In the Table, "—" represents no presence of a relevant hydrogen atom; "Ph" means a carbon atom in an aromatic ring; and "C1 to C7" represent the carbon atom numbered in the order from a carbon atom close bonded to an aromatic ring. The numbers in the Table show deuteration rate of the hydrogen atom bonded to each carbon atom (the same hereinafter).

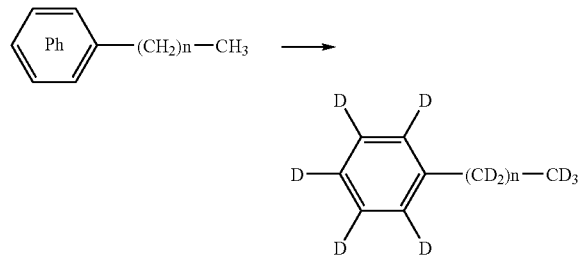

Examples 9 to 12

Deuteration was carried out by the same procedure as in Example 1, except for using the compounds shown in Table 3 as substrates. Deuteration rate (%) of the hydrogen atom bonded to the carbon atom in the compound is shown in Table 3.

TABLE 3

| | Substrate | Ph | C1 | C2 | C3 | C4 | C5 | Terminal H |
|---|---|---|---|---|---|---|---|---|
| Example 9 | Ph(CH$_2$)$_2$COOH | 0 | 91 | 77 | — | — | — | 100 |
| Example 10 | Ph(CH$_2$)$_3$COOH | 33 | 96 | 97 | 55 | — | — | 100 |
| Example 11 | Ph(CH$_2$)$_4$COOH | 26 | 97 | | 80 | 0 | — | 100 |
| Example 12 | Ph(CH$_2$)$_5$COOH | 21 | 94 | (A) | 81 | (B) | 0 | 100 |

* (A) + (B) = 60%

In the Table, "terminal H" means a hydrogen atom in a carboxyl group. The numbers in the Table show deuteration rate thereof.

Example 13

Deuteration was carried out by the same procedure as in Example 1, except for using the compounds shown in Table 4 as substrates. Deuteration rate (%) of the hydrogen atom bonded to the carbon atom in the compound is shown in Table 4.

TABLE 4

| | Substrate | Ph | C1 | C2 + C3 | C4 | C5 |
|---|---|---|---|---|---|---|
| Example 13 | Ph(CH$_2$)$_4$COOCH$_3$ | 0 | 90 | 91 | 0 | 0 |

In the Table, "Ph", "C1", "C2", "C3", "C4" and "C5" represent the carbon atoms denoted by the number in the following formula, respectively.

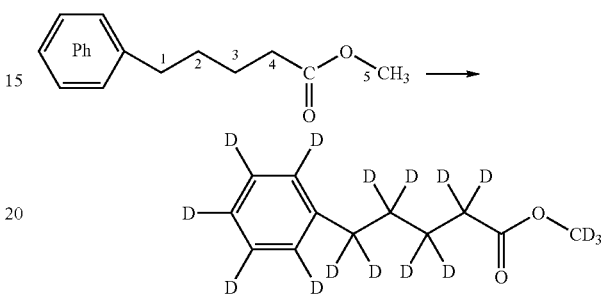

Examples 14 to 16

Deuteration was carried out by the same procedure as in Example 1, except for using the compounds shown in Table 5 as substrates. Deuteration rate (%) of the hydrogen atom bonded to the carbon atom in the compound is shown in Table 5.

TABLE 5

| | Substrate | Ph | C1 | C2 | C3 | C4 | C5 |
|---|---|---|---|---|---|---|---|
| Example 14 | Ph(CH$_2$)$_3$OH | 0 | 92 | 31 | 0 | — | — |
| Example 15 | Ph(CH$_2$)$_4$OH | 0 | 90 | 24 | 32 | 0 | — |
| Example 16 | Ph(CH$_2$)$_5$OH | 0 | 89 | (A) | 39 | (B) | 0 |

* (A) + (B) = 42%

Examples 17 and 18

Deuteration was carried out by the same procedure as in Example 1, except for using the compounds shown by the following formula as substrates. Deuteration rate (%) of the hydrogen atom bonded to the carbon atom in the compound is shown in Table 6.

TABLE 6

| | Substrate | Ph | C1 | C2 | C3 | C4 | C5 |
|---|---|---|---|---|---|---|---|
| Example 17 | Ph(CH$_2$)$_3$OCH$_3$ | 0 | 91 | 88 | 0 | 0 | — |
| Example 18 | Ph(CH$_2$)$_3$OCH$_2$CH$_3$ | 0 | 96 | 99 | 0 | 0 | 0 |

Comparative Examples 4 and 5

Deuteration was carried out by the same procedure as in Example 1, except for using the compounds shown by the following for mula as substrates, however, deuteration of any compound did not occur at all.

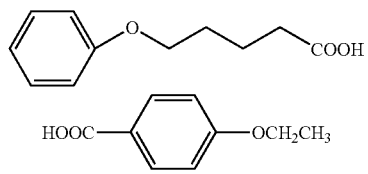

Examples 19 to 24

Deuteration was carried out by the same procedure as in Example 1, except for using the compounds shown the following formula as substrates in the amount shown in the Table below. Deuteration rate (%) of the hydrogen atom bonded to the carbon atom in the compound is shown in Table 7. X represents a substituent shown in Table 7.

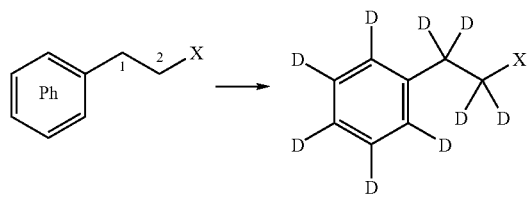

TABLE 7

| | Substituent (X) | Amount of substrate | Ph | C1 | C2 | Terminal CH₃ |
|---|---|---|---|---|---|---|
| Example 19 | H | 4 mmol | 0 | 59 | 52 | — |
| Example 20 | CH₃ | 4 mmol | 19 | 77 | 75 | 56 |
| Example 21 | OCH₃ | 0.25 mmol | 0 | 85 | 7 | 0 |
| Example 22 | NHCOCH₃ | 0.25 mmol | 15 | 92 | 38 | 0 |
| Example 23 | COOH | 0.25 mmol | 0 | 91 | 77 | *Terminal H 100% |
| Example 24 | COCH₃ | 0.25 mmol | 36 | 100 | 100 | 96 |

Examples 25 to 30

Deuteration was carried out by the same procedure as in Example 1, except for using the compounds shown in Table 8 as substrates in the amount in the following table. Deuteration rate (%) of the hydrogen atom bonded to the carbon atom in the compound is shown in Table 8.

TABLE 8

| | Substrate | Product | Amount of substrate | Deuteration rate |
|---|---|---|---|---|
| Exam. 25 | Ph–CH₃ | Ph–CD₃ | 5 mmol | 64% |
| Exam. 26 | Ph–C₆H₄–CH₃ | Ph–C₆H₄–CD₃ | 0.25 mmol | 94% |
| Exam. 27 | PhCH₂–C₆H₄–CH₃ | PhCH₂–C₆H₄–CD₃ | 0.25 mmol | 92% |
| Exam. 28 | H₃CO–C₆H₄–CH₃ | H₃CO–C₆H₄–CD₃ | 3 mmol | 81% |
| Exam. 29 | O₂N–C₆H₄–CH₃ | H₂N–C₆H₂D₂–CD₃ | 0.25 mmol | 95% *deuteration rate of an aromatic ring: 56% |

TABLE 8-continued

| Substrate | Product | Amount of substrate | Deuteration rate |
|---|---|---|---|
| Exam. 30 H$_2$N—C$_6$H$_4$—CH$_3$ | D-substituted H$_2$N—C$_6$H$_2$D$_2$—CD$_3$ | 0.25 mmol | 92% *deuteration rate of an aromatic ring: 63% |

Examples 31 to 33

Deuteration was carried out by the same procedure as in Example 1, except for using the compounds shown in Table 9 substrates, using deuterated methanol as a reaction solvent instead of deuterium oxide, and conducting the reaction at 80° C. Deuteration rate (%) of the hydrogen atom bonded to the carbon atom in the compound is shown in Table 9.

TABLE 9

| Substrate | | Ph | C1 | C2 | C3 | C4 | C5 |
|---|---|---|---|---|---|---|---|
| Example 31 | Ph(CH$_2$)$_2$CH$_3$ | 0 | 59 | 26 | 4 | — | — |
| Example 32 | Ph(CH$_2$)$_3$CH$_3$ | 0 | 73 | 69 | 10 | 0 | — |
| Example 33 | Ph(CH$_2$)$_4$CH$_3$ | 0 | 81 | 70 | 10 | | 5 |

Example 34

Deuteration was carried out by the same procedure as in Example 1, except for using ibuprofen represented by the following formula as substrate. Deuteration rate (%) is shown in Table 10.

TABLE 10

(H$_3$C)$_2$CH-CH$_2$(2)-C$_6$H$_4$-CH(3)(CH$_3$)-COOH, positions labeled 1, 2, 3, 4

| | C1 | C2 | C3 | C4 | Terminal H |
|---|---|---|---|---|---|
| Example 34 | 50 | 96 | 94 | 50 | 100 |
| Comparative Example 6 | 0 | 1 | 18 | 0 | 100 |

Comparative Example 6

Deuteration was carried out by the same procedure as in Example 34, except for carrying out a reaction at room temperature. Deuteration rate (%) is shown in Table 10.

As is clear from comparison of deuteration rates between Example 1 and Comparative Example 1 and between Example 34 and Comparative Example 6, although in case of the deuteration reaction at room temperature, a hydrogen atom of a carbon atom only at a benzyl position can be deuterated slightly, the deuteration reaction under reflux can deuterate a hydrogen atom bonded to not only alkyl carbon at a benzyl position but also other than at a benzyl position at high rate.

Further, it is clear from the results of Comparative Examples 2 and 3 that an aliphatic compound having no aromatic ring cannot be deuterated Furthermore, as is clear from the results of Examples 2 to 8 and 31 to 33, deuteration rate of a hydrogen atom bonded to a carbon atom at far position from an aromatic ring becomes lower, according as the number of carbon atoms of alkyl group directly bonded to an aromatic ring increases.

It is clear from the results of Examples 2 to 8, 17, 18, 25 to 28 and 31 to 33, that even a compound showing low solubility in a deuterated solvent can be deuterated by a method for deuteration of the present invention.

Further, as is clear from Examples 17 and 18, in the case of an aromatic compound containing an oxygen atom in the alkyl chain, it is difficult to deuterate a hydrogen atom bonded to a carbon atom next to the oxygen atom and a hydrogen atom of a carbon atom at far position from said oxygen atom viewed from an aromatic ring.

INDUSTIAL APPLICABILITY

By the method of the present invention, characterized by reaction of a compound containing a methyl group or an alkylene group having not less than 2 carbon atoms directly bonded to an aromatic ring which may have a substituent, and a deuterated solvent in the presence of an activated palladium carbon catalyst under sealed reflux condition, a hydrogen atom of said methyl group, which could be deuterated but at low deuteration rate by a conventional method, can be deuterated very effectively, and further deuteration of not only a hydrogen atom at a benzyl position in an alkylene group having not less than 2 carbon atoms but also a hydrogen atom other than at a benzyl position, whose deuteration were impossible by a conventional method, is now possible.

What is claimed is:

1. A method for replacing with deuterium a hydrogen atom of a methyl group or a hydrogen atom bonded to a carbon atom at a benzyl position and the other carbon atoms of an alkylene group having not less than 2 carbon atoms, in a compound containing the methyl group or the alkylene group having not less than 2 carbon atoms, directly bonded to an aromatic ring which may have a substituent, which comprises placing said compound in a deuterated solvent in the presence of activated palladium carbon, under sealed reflux condition.

2. The method for replacing with deuterium according to claim 1, wherein said compound containing the methyl group or the alkylene group having not less than 2 carbon atoms, directly bonded to the aromatic ring which may have the substituent is a compound having said methyl group.

3. The method for replacing with deuterium according to claim 1, wherein said compound containing the methyl group or the alkylene group having not less than 2 carbon atoms, directly bonded to the aromatic ring which may have the substituent, is a compound containing said alkylene group having not less than 2 carbon atoms, directly bonded to the aromatic ring which may have a substituent.

4. The method for replacing with deuterium according to claim 1, wherein said compound containing the methyl group or the alkylene group having not less than 2 carbon atoms, directly bonded to the aromatic ring, in said compound containing the methyl group or the alkylene group having not less than 2 carbon atoms, directly bonded to the aromatic ring which may have the substituent, is a compound represented by the general formula [1]:

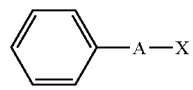

(wherein A is a methylene group or an alkylene group having not less than 2 carbon atoms; and X is a hydrogen atom, an alkoxy group, a carboxyl group, a hydroxyl group, an amino group, an acyl group, an acylamino group or an alkoxycarbonyl group; and when A is a methylene group, X is a hydrogen atom).

5. The method for replacing with deuterium according to claim 4, wherein the alkylene group having not less than 2 carbon atoms, represented by A is a straight chained alkylene group and X is a hydrogen atom, a carboxyl group, an acyl group, an acylamino group or an alkoxycarbonyl group.

6. The method for replacing with deuterium according to claim 4, wherein the alkylene group having not less than 2 carbon atoms, represented by A is a straight chained alkylene group having not less than 3 carbon atoms and X is an alkoxy group, a hydroxyl group or an amino group.

7. The method for replacing with deuterium according to claim 1, wherein the substituent, which an aromatic ring may have, is one selected from the group consisting of an alkyl group, an aryl group, an aralkyl group, an alkoxy group, a nitro group and an amino group.

* * * * *